(12) United States Patent
Guegel-Wild et al.

(10) Patent No.: US 12,127,859 B2
(45) Date of Patent: Oct. 29, 2024

(54) COMMUNICATION SYSTEM AND METHOD FOR A MEDICAL IMAGING SYSTEM

(71) Applicant: Siemens Healthineers AG, Forchheim (DE)

(72) Inventors: Stefanie Guegel-Wild, Langensendelbach (DE); Stephan Nufer, Erlangen (DE); Stefan Kiesel, Hausen (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 17/869,098

(22) Filed: Jul. 20, 2022

(65) Prior Publication Data

US 2023/0028796 A1    Jan. 26, 2023

(30) Foreign Application Priority Data

Jul. 23, 2021   (EP) .................................. 21187363

(51) Int. Cl.
*A61B 5/00* (2006.01)
*G08B 5/36* (2006.01)
(52) U.S. Cl.
CPC ................ *A61B 5/742* (2013.01); *G08B 5/36* (2013.01)
(58) Field of Classification Search
CPC .................................. A61B 5/742; G08B 5/36
USPC .................................................... 340/815.69
See application file for complete search history.

(56) References Cited

U.S. PATENT DOCUMENTS

| 2008/0021329 | A1  | 1/2008 | Luciano et al. |
| 2011/0058646 | A1* | 3/2011 | Herranz ................. G01N 23/04 250/361 R |
| 2015/0126865 | A1  | 5/2015 | Murai et al. |
| 2017/0050046 | A1* | 2/2017 | Walder .................... A61N 5/062 |
| 2017/0138545 | A1* | 5/2017 | Minor ........................ F21K 9/61 |
| 2019/0143145 | A1* | 5/2019 | Laurence, Jr. ........ A61N 5/1081 600/1 |
| 2020/0222711 | A1* | 7/2020 | Walder ................. A61N 5/1071 |
| 2020/0337655 | A9  | 10/2020 | Lu et al. |

FOREIGN PATENT DOCUMENTS

WO    WO 2020182279 A1    9/2020

* cited by examiner

*Primary Examiner* — Jack K Wang
(74) *Attorney, Agent, or Firm* — Harness, Dickey & Pierce, P.L.C.

(57) ABSTRACT

At least one example embodiment provides a communication system for a medical imaging system. The system includes a data interface configured to receive event-data from the medical imaging system; a control unit configured to provide a light pattern from a number of light patterns based on the event-data, wherein for different types of event-data different types of light patterns are provided; and an illumination unit comprising a linear arrangement of multiple light sources, the control unit being configured to control the multiple light sources to emit a changing light pattern from the number of light patterns.

21 Claims, 3 Drawing Sheets

COMMUNICATION SYSTEM AND METHOD FOR A MEDICAL IMAGING SYSTEM

CROSS-REFERENCE TO RELATED APPLICATION(S)

The present application claims priority under 35 U.S.C. § 119 to European Patent Application No. EP 21187363.3, filed Jul. 23, 2021, the entire contents of which are incorporated herein by reference.

FIELD

Some example embodiments of the present invention relate to a communication system and a communication method for a medical imaging system, such as for Intelligent light visualization to support the acquisition workflow.

BACKGROUND

For operators of imaging systems such as magnetic resonance imaging (MRI) systems, computed tomography (CT) systems, X-ray systems, ultrasound (US) systems, etc., it is often difficult to recognize certain events occurring on the system or during examinations with such systems. On the one hand, there are events that are triggered automatically, for example by voice output from intelligent assistants, or when a threshold value is reached or an automatic movement occurs. On the other hand, there are events that are triggered indirectly or directly by an operator or a patient.

Depending on the nature of an event, it is important or sometimes indispensable to react on such event with the appropriate actions. However, such events typically do not occur during calm and patient situations, but in hectic everyday clinical practice. Operators of such systems have to particularly share their attention with the patient, other clinical staff and, if necessary, other people involved.

SUMMARY

This could be solved by text messages indicating that an event has occurred, such as "Scan is triggered in a few seconds", "Patient alarm is active", or "Table is moving and this area should be kept clear". In praxis, there are already some events, such as "active patient alarm" that are outputted via a display that is attached to the scanner, as well as a loudspeaker in the room or the administration of contrast media, in which the information is provided via a display or a lamp.

Until now, there are no messages indicating automatic table movements or active voice output.

At least one example embodiment of the present improves the known systems, devices and methods to facilitate an improvement in data communication for a medical imaging system, especially in order to communicate events from such modality to a user.

This is achieved by a communication system according to claim 1, a communication method according to claim 10 and a medical imaging system according to claim 13.

According to at least one example embodiment, a communication system for a medical imaging system comprises a data interface configured to receive event-data from the medical imaging system; a control unit configured to provide a light pattern from a number of light patterns based on the event-data, wherein for different types of event-data different types of light patterns are provided; and an illumination unit comprising a linear arrangement of multiple light sources, the control unit being configured to control the multiple light sources to emit a changing light pattern from the number of light patterns.

According to at least one example embodiment, the control unit is configured to control an intensity of individual light sources of the multiple light sources, wherein at least one of (i) the illumination unit configured to emit different colors and the control unit is configured to control an intensity of individual colors of the multiple light sources or (ii) the control unit is configured to provide two or more light patterns at a same time.

According to at least one example embodiment, the control unit is configured to assign an individual light pattern to one or more types of event-data, the event data being associated with at least one of an automatic sound output being provided to an operator or a patient examined by the medical imaging system, physiological data, times or phases of an examination, errors, alarms or emergencies, a feedback to inputs of a user, or an indication of events automatically started.

According to at least one example embodiment, the control unit comprises at least one of a mapping table identifying an allocation of light patterns to types of event-data, or a machine learning model trained for providing individual light patterns for the types of event-data.

According to at least one example embodiment, the control unit is configured to vary the light patterns based on quantitative values of the event-data.

According to at least one example embodiment, the illumination unit is flexible or shaped such that the illumination unit is configured to be arranged on an outer surface of the medical imaging system.

According to at least one example embodiment, the system further includes an ambient light sensor, the control unit being configured to control a brightness of a light pattern based on measurements of the ambient light sensor.

According to at least one example embodiment, the system further includes a number of additional light sources configured to illuminate areas of the medical imaging system, the areas including an area of a patient table of the medical imaging system or an area adjacent to a patient table of the medical imaging system.

According to at least one example embodiment, the system further includes an acoustic output module configured to at least one of emit sound patterns or artificial announcements, wherein the control unit is configured to provide the at least one of sound patterns or artificial announcements based on at least one of (i) the event-data or (ii) the provided light pattern.

According to at least one example embodiment, a method comprises receiving the event-data from the medical imaging system; identifying the type of the event-data; providing the light pattern based on the identified type of event-data; and outputting the light pattern with the illumination unit.

According to at least one example embodiment, the method further includes identifying at least one quantitative value of the event-data; and modifying the provided light pattern according to the identified value.

According to at least one example embodiment, an individual light pattern is provided in at least one of the cases a patient listens to a message, a message is outputted to a user, physiological signals are received, a countdown is running, a contrast agent is applied to a patient, stages of an examination are reached, an emergency or alarm occurs, a user-input or a change of preferences occurs, a movement of parts of the medical imaging system is initialized, occurring or finished, or actions automatically performed by the medical imaging system occur.

According to at least one example embodiment, a medical imaging system includes a communication system according to at least one example embodiment.

According to at least one example embodiment, a computer-readable medium includes a computer program that, when executed by a computing system or a control device for a medical imaging system, causes the computing system or the control device to perform a method according to at least one example embodiment.

BRIEF DESCRIPTION OF THE DRAWINGS

Other objects and features of example embodiments of the present invention will become apparent from the following detailed descriptions considered in conjunction with the accompanying drawings. It is to be understood, however, that the drawings are designed solely for the purposes of illustration and not as a definition of the limits of the present invention.

In the diagrams, like numbers refer to like objects throughout. Objects in the diagrams are not necessarily drawn to scale.

DETAILED DESCRIPTION

Figure 1:
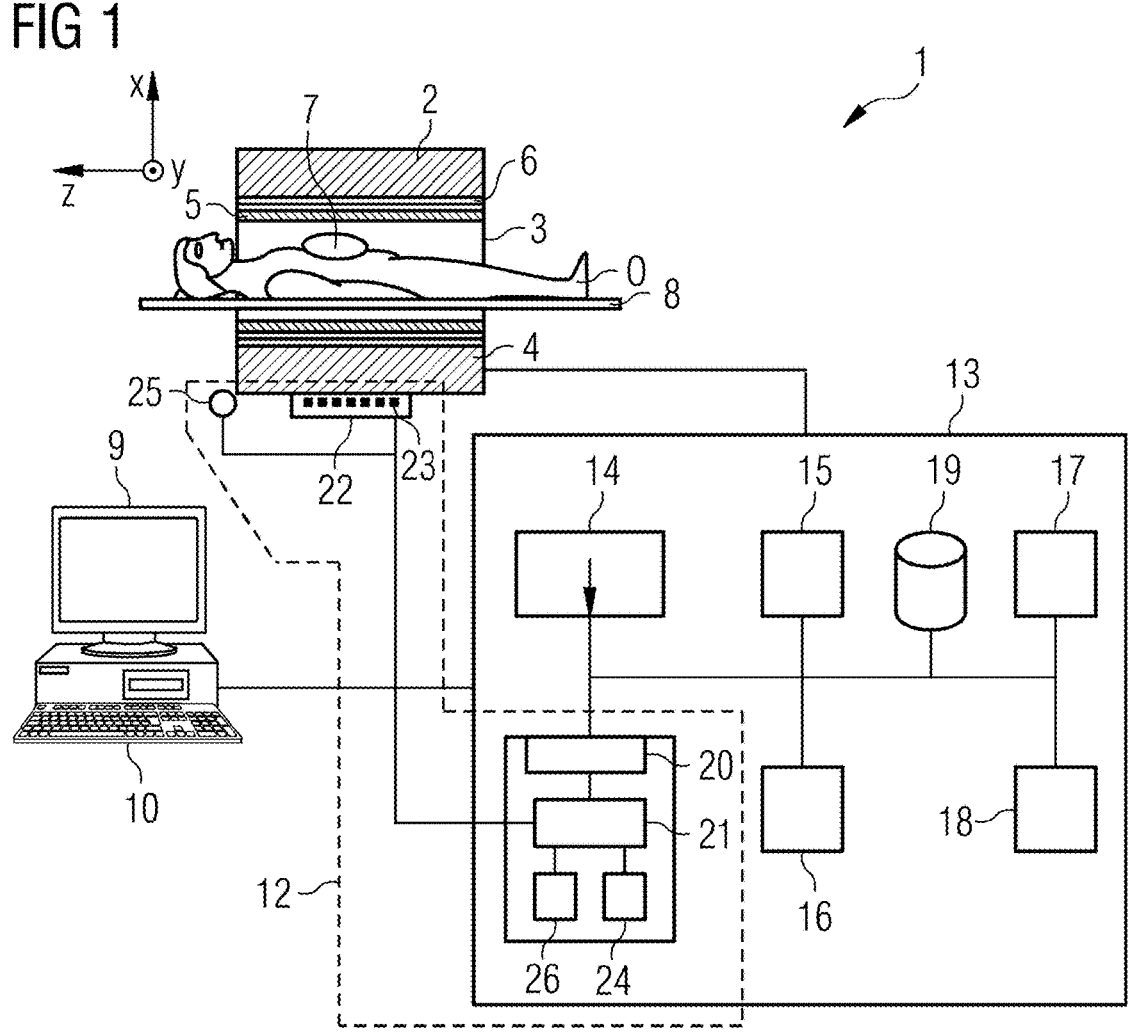
FIG. 1 shows a simplified MRI system according to an embodiment of the present invention.

A communication system according to at least one example embodiment of the present invention is suitable for medical imaging systems. This means that is able to communicate with such medical imaging systems and "understand" respective protocols used for data communication or for data management of such medical imaging systems. Preferred medical imaging systems are systems for examining a patient from the outside (thus, especially no endoscopes are meant), comprising an examination architecture surrounding an examination area at least partially. Such medical imaging systems are especially magnetic resonance imaging (MRI) systems, computed tomography (CT) systems, X-ray systems or ultrasound (US) systems. The communication system comprises the following components:
- a data interface designed for receiving event-data from the medical imaging system,
- a control unit designed to provide a light pattern from a number of light patterns based on the event-data, wherein for different types of event-data different types of light patterns are provided,
- an illumination unit comprising a linear arrangement of multiple light sources that are controlled by the control unit in order to emit a changing light pattern provided by the control unit.

The communication method according to at least one example embodiment of the present invention for a communication system according to at least one example embodiment of the present invention, especially for a medical imaging system with such communication system, comprises the following steps:
- receiving event-data from a medical imaging system,
- identifying the type of the event-data,
- providing a light pattern depending on the identified type of event-data,
- outputting the light pattern with the illumination unit.

The data interface must be able to communicate with the medical imaging system in order to receive the event-data. Suitable interfaces are well known in the art and could be internal data buses, USB-interfaces or interfaces used to interchange medical data or control data for the medical imaging system.

Event-data is data concerning an occurring event. Such event-data is, e.g., data referring to an action or occurrence in the workflow of the medical imaging system, but not image data recorded during an examination. Generally, one can say that event-data is data referring to the environment of an examination (and could theoretically be any data that is not examination data, itself). Such actions or occurrences are preferably events selected from the group comprising sending user inputs (e.g. for control or changing of preferences) to a medical imaging system, actions of a medical imaging system (e.g. movement of motors, output of information or starting of data acquisition) and measured parameters (e.g. breath or heartbeat). But also other data of a patient that are relating to an examination could be event data, especially physiological data and/or data of movements of a patient and/or data actively outputted by a patient (e.g. speech or other sounds).

The control unit is managing the complete operation of the communication system. This comprises the processing of the event-data and the output of light patterns to the illumination unit. In order to be able to provide different types of light patterns for different types of event-data, the control unit is designed for detecting the type of event-data. The expression "type" here means to which classification of event the event-data belongs. Generally, one can say that the type reflects a certain parameter (especially independent of its actual value). In the case of data referring to measurements of a sensor (e.g. heartbeat-sensor or breathing-sensor, sensors for pulsoxymetry, or sensors for measuring stimuli of nerves, etc.), the event type may be "sensor data", especially itemized to the sort of sensor (e.g. "heartbeat-sensor-data" or "breathing-sensor-data", etc.). In the case of data referring to user inputs received by the medical imaging system, the type may be "user input", preferably itemized to the sort of user input (e.g. control-data or preference-data). In the case of data referring to actions of the medical imaging systems, the event type may be "machine actions", especially itemized to the sort of action (e.g. movement-data, feedback-data, output-indicating-data, start of actions-data, performing or progressing of actions-data or finished actions-data).

After the type is determined, the control unit is also designed to provide a suitable light pattern for the determined type. The expression "providing" here means generating or selecting, since a suitable pattern could be selected (e.g. from a table with types of event-data assigned to light patterns) or generated (e.g. by an algorithm further processing the event-data). There are multiple (at least more than two but especially even more) light patterns possible in order to characterize different types. The control unit preferably chooses between these light patterns (e.g. from said list) or uses them as basic light patterns to generate a resulting light pattern (e.g. with said algorithm).

The illumination unit comprises multiple light sources, e.g. light emitting diodes (LED). Although the light sources may be monochrome light sources, it is particularly preferred that they are colored, e.g. RGB-LED. It is important that the light sources could be controlled individually, in order to emit (changing) light patterns. In order to control brightness of light sources, voltage or current of the light sources could be controlled or pulse width modulation (PWM) signals could be applied. Such control is well known in the art. It is clear that the control unit controls the illumination unit by applying the light pattern. This could happen by applying the light pattern to an internal controller of the illumination unit that controls the single light sources or by applying control signals from the control unit to the light sources directly. It should be noted that the illumination unit is no display of the medical imaging device, but a separate unit.

It should also be noted that light patterns in the sense of at least one example embodiment of the present invention are abstract light patterns, especially not including letters or numerics, but changing patterns of brighter or dimmer light distributions over the light sources of the illumination unit, especially with patterns of (especially changing) different colors. Thus, a light pattern is a spatially and/or temporally changing (especially chatoyant) light distribution. While emitting the light pattern, different light sources of the illumination unit are controlled such that they emit a different brightness, wherein the brightness of a number of single light sources changes over time, such that a spatially and/or temporally changing light pattern is emitted. Preferably, at least one of the light patterns is colored, especially wherein the brightness of a number of basic colors (e.g. red, green and blue) is changing spatially and/or temporally.

There is also the possibility to output two or more light patterns, especially by merging or superposing these light patterns or split the illumination unit into sections displaying different light patterns. A preferred illumination unit is split into a first (e.g. smaller) section for visualizing lasting events and a second (e.g. bigger) section for exceptional events. For example, is breathing of the patient shown in a first section of the illumination unit and alarm be shown in a second section of the illumination unit. Alternatively or additionally may the brightness be an indicator of a first event and color the indicator of another event. For example, breathing could be shown by dimming the illumination unit according to the breath and a countdown may be shown by coloring the light output of this illumination unit from red over yellow to green. It is also possible to visualize this countdown with an increasing or a decreasing number of light emitters of the illumination unit and a breath signal by dimming or changing colors.

At least one example embodiment of the present invention is to provide a communication channel for the medical imaging device in form of "intelligent lights" (i.e. the light patterns) that build a bridge between user and imaging system. For example, when the imaging system outputs an audio message, a light pattern could visually enhance the understanding of the audio message, at least when the meaning of the light pattern (the connection to an event) is known by the user. Additionally, the light pattern outs a focus on a medical imaging system when an event has occurred.

Especially, a light pattern according to at least one example embodiment of the present invention could advantageously improve the following situations.

A) It could indicate that the system is emitting an automatic (voice) message to the user. With a light pattern, there is an accentuation from where the message origins. However, it could also indicate that a patient is listening to an automated voice message from a digital assistant of the imaging system through headphones. Since only the patient wears the headphones and hears the audio output, an operator would know that the patient is currently hearing an automatic message and does not speak to the patient during this time in order to reduce further, unnecessary stress for the patient.

B) It could translate physiological signals, e.g. from a breathing sensor, into light patterns. This informs an operator about physical conditions of a patient, e.g. the patient's breathing rate: whether breath is steadily, too quickly or irregularly. Especially, during examination steps in which patients are supposed to hold their breath, there could also be visual feedback as to whether the patient actually holds the breath or not. Thus, on the one hand, the light patterns bring transparency to the breathing rate and visual feedback on the patient's cooperation with breathing commands. The light patterns have the additional advantage that an operator places a greater focus on the patient or the patient's well-being.

D) It could enhance transparency of a process, e.g. a scan with a countdown could be visualized by the communication system. The light pattern could also give an operator additional feedback about the process that has just started and/or visualize the time remaining until the end of the process. This has the advantage that a near occurrence could be visualized (e.g. in order to leave the room) or time remaining until finish or change of a process. For example, concerning a process such as "contrast agent injection", a light pattern could indicate the start and end of the process via a progression animation. This allows operators to see that the administration of contrast agent has started and when it should be finished.

E) It could visualize alarm states, especially in the case there is a problem with the administration of contrast agent. In the case an injector of contrast agent reports an error or the patient has triggered the patient alarm, the light pattern could be changed (e.g. from the light pattern for "contrast agent injection" to the light pattern "alarm") and then e.g. show a red flashing instead of a progression.

F) It could give feedback for reactions of the medical imaging system according to actions of the operator. For example, if a patient table is manually moved into the Isocenter by the operator, a short light pattern (especially combined with a noise) could give the operator feedback that the desired position has been reached.

G) It could indicate actions that were started automatically by the medical imaging system. For example, if a sensor such as a 3D camera or EKG sensors are currently in detection mode, this could be communicated with a first light pattern and if the action was successful, briefly confirmed with a second light pattern (and especially also with a sound or with a display at the system). In the case the action was unsuccessful, a third light pattern could be outputted to indicate a failure.

A control device according to at least one example embodiment of the present invention for controlling a medical imaging system comprises a system according to at least one example embodiment of the present invention. Alternatively or additionally it is designed to perform the method according to at least one example embodiment of the present invention. The control device may comprise additional units or devices for controlling components of the medical imaging system, e.g. for a magnetic resonance imaging system, the control device may comprise a sequence control unit for measurement sequence control, a memory, a radio-frequency transmission device that generates, amplifies and transmits RF pulses, a gradient system interface, a radio-frequency reception device to acquire magnetic resonance signals and/or a reconstruction unit to reconstruct magnetic resonance image data.

A medical imaging system according to at least one example embodiment of the present invention, especially with an at least partially enclosed examination area, comprises a communication system according to at least one example embodiment of the present invention and is preferably designed to perform a communication method according to at least one example embodiment of the present invention. It is preferred that the illumination unit of the communication system is arranged on the outer surface of the medical imaging system such that the illumination unit is following the outer shape of the medical imaging system. The medical imaging system preferably being a magnetic resonance imaging system, a computer tomography system, an X-ray system or an ultrasound system.

Some units or modules of the communication system mentioned above can be completely or partially realized as software modules running on a processor of a computing system, especially of a control device. A realization largely in the form of software modules can have the advantage that applications already installed on an existing system can be updated, with relatively little effort, to install and run these units of the present application. The object of at least one example embodiment of the present invention is also achieved by a computer program product with a computer program that is directly loadable into the memory of a computing system, and which comprises program units to perform the steps of the inventive method when the program is executed by the computing system. In addition to the computer program, such a computer program product can also comprise further parts such as documentation and/or additional components, also hardware components such as a hardware key (dongle etc.) to facilitate access to the software.

A computer readable medium such as a memory stick, a hard-disk or other transportable or permanently-installed carrier can serve to transport and/or to store the executable parts of the computer program product so that these can be read from a processor unit of a computing system. A processor unit can comprise one or more microprocessors or their equivalents.

Particularly advantageous embodiments and features of at least one example embodiment of the present invention are given by the dependent claims, as revealed in the following description. Features of different claim categories may be combined as appropriate to give further embodiments not described herein.

According to a preferred embodiment of the communication system, the control unit is designed to control the intensity of individual light sources of the illumination unit. This means that the brightness of the light sources can be controlled for the individual light sources. As already explained above, brightness could be controlled via voltage, current or PWM signals. This control of brightness does not refer to turning the light sources on and off, but dimming the light sources to a certain brightness level, and especially changing this brightness levels of the light sources over time depending on the provided light pattern.

It is preferred that the illumination unit is designed for emitting different colors. To achieve that, the control unit is preferably designed to control the intensity of individual colors of the light sources. This means controlling the emission of different colors of a light source that are able to emit different colors, e.g. preferred RGB-LEDs, or to control the brightness of light sources having different colors. The brightness of different colors could be controlled via voltage, current or PWM signals.

Thus, such preferred embodiment is designed to produce changing light patterns, where brightness and especially also color changes and produce the sensation of a moving and/or chatoyant light pattern.

According to a preferred embodiment of the communication system, the control unit is designed to assign an individual light pattern to multiple event-data types. This means that for each type of the different types of event-data, an individual type of light pattern is assigned. The provision of light patterns is depending on the assignment. For a certain type of event-data, the very light pattern that is assigned to this type is chosen.

The types of event-data (one or more) can be chosen from the following group:

One type is indicating that an automatic sound output is provided to an operator or a patient examined by the medical imaging system.

One type is physiological data, especially measurements of breath sensors or heartbeat sensors.

One type indicates times or phases of an examination, especially countdowns or data about certain examination steps, e.g. injection of a contrast agent.

One type comprises errors, alarms or emergencies.

One type is event-data concerning feedback to inputs of a user.

One type is an indication of events automatically started by the medical imaging system.

Each of these types could be further segmented into sub-types (also being regarded to be types of event-data). For example, could one type be errors, one other type be emergencies (here: something bad happened) and one type be alarms (here: a possible dangerous situation occurs), or one type be alerts (indicating that a possibly dangerous action is going to be started, such as e.g. the start of an MRT measurement or start a movement of the patient). To each of these (sub-) types a different light pattern could be assigned.

According to a preferred embodiment, the control unit comprises a mapping table with an allocation of light patterns to certain types of event-data. Thus, a light pattern is selected from this mapping table and applied to the illumination unit.

According to a preferred embodiment, the control unit comprises a machine learning model trained for providing individual light patterns for certain types of event-data. Thus, a light pattern could be selected from the "feature" of the result of the model with the highest score. However, the model could also generate an individual light pattern for each input such that for different types of event-data the light patterns are different and for similar types of event-data, the light patterns are similar.

According to a preferred embodiment of the communication system, light patterns are additionally varied based on quantitative values of the event-data. It is preferred that the control unit is designed to achieve that. This could be achieved with the following preferred steps:

identifying at least one quantitative value of the event-data, e.g. a parameter value, modifying a provided light pattern according to the identified value.

For example, concerning a light pattern referring to the signal to a breath sensor, stronger breathing movements could be indicated with brighter lights or different colors.

The variation of a light pattern is here depending on the values of measurements of the sensor.

Concerning a workflow-dependent output of sound-files to the patient, the type of light patterns for different sound-files may be the same, but the patterns preferably variate a little bit indicating, what sound-file is played at the very moment.

Thus, it is preferred that the basic nature of a light pattern is the same, but variations are made concerning brightness, speed of changes or color maps.

According to a preferred embodiment of the communication system, the illumination unit is flexible or shaped such that it can be arranged on the outer surface of a medical imaging system, especially following outer contours of the medical imaging system when arranged on it. It could also be arranged on a user-monitor, e.g. a patient surveillance monitor.

It should be noted that the feature of linearity of the illumination unit does not mean that the illumination unit is inevitably a rigid straight line. It generally could be rigid, elastic or flexible. Independently from that, it may be shaped in a straight or curved line or even a circle, run in curves or corners, even in spirals or a sinus line. However, it is preferred that it follows the contours of the medical imaging system, e.g., a plane or an edge of the imaging system.

According to a preferred embodiment the communication system comprises an ambient light sensor. Such ambient light sensor measures the brightness of the surrounding light. The control unit is designed to control a basic brightness of a light pattern depending on measurements of the ambient light sensor. Preferably, the basic brightness is darker when the room is dark and brighter when the room is well lighted. It should be noted that the pattern itself is not changed, but a general brightness level. This has the advantage that the light patterns are adaptive concerning the illumination of the room where the communication system is arranged. Thus, a preferred communication system is designed to do light adjustments depending on the light situation within the examination room.

According to a preferred embodiment, the communication system comprises an additional number of light sources designed and arranged to illuminate certain areas of the medical imaging system, preferably an area of or adjacent to a patient table of the medical imaging system. For example, concerning mechanical movements of components of the medical imaging system (e.g. the patient table) the danger area (e.g. the area to where the table could move) is illuminated by the additional light source. This has the advantage that the attention of the user is directed to the respective area. An operator then may stop or change the movement of the patient table in the case of an emergency.

According to a preferred embodiment, the communication system additionally comprises an acoustic output module designed to emit sound patterns and/or announcements, especially artificial, announcements. Preferably, the control unit is designed to provide (i.e. generate or select) these sound patterns and/or announcements based on the event-data and/or the provided light pattern. This has the advantage that the light pattern can better be perceived when accompanied by a sound pattern. A sound pattern can me provided using the same method as for providing a light pattern.

According to a preferred embodiment of the communication method, an individual light pattern is provided in one or more of the following cases:
a patient listens to a message, especially an automatically outputted message and/or
a message is outputted to a user and/or
physiological signals, especially of a breath sensor or a heart sensor, are received and/or
a countdown is running and/or
a contrast agent is applied to a patient and/or
certain stages of an examination are reached and/or
an emergency or alarm occurs and/or
a user-input or a change of preferences happened and/or
a movement of parts of the medical imaging system is initialized, happening or finished and/or
actions automatically performed by the medical imaging system happen.

FIG. 1 shows a schematic representation of a medical imaging system 1 in form of a magnetic resonance imaging system ("MRI-system" 1). The MRI system 1 includes the actual magnetic resonance scanner (data acquisition unit) 2 with an examination space 3 or patient tunnel in which a patient or test person is positioned on a driven bed 8, in whose body the actual examination object O is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, example embodiments can also be used at other MRI systems, for example with a laterally open, C-shaped housing, as well as in smaller magnetic resonance scanners in which only one body part can be positioned.

Furthermore, the MRI system 1 has a central control device 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence or, respectively, a series of multiple pulse sequence to acquire magnetic resonance images within a measurement session. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device 17 (likewise communicating with the sequence control unit 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit 9, and measurements can be planned and started by the input unit (possibly in combination with the display unit 9), and in particular suitable control protocols can be selected (and possibly modified) with suitable series of pulse sequence as explained above.

The control device 13 comprises parts of a communication system 12 designed to perform the communication method according to at least one example embodiment of the present invention. This communication system 12 comprises the following components.

A data interface 20 designed for receiving event-data E from the medical imaging system 1. This data interface 20 may be a software module in the control device 13. The control device is configured such that the data interface has access to event-data of the control device.

A control unit 21 designed to provide a light pattern P from a number of light patterns P based on the event-data E. This control unit 21 may also be a software module in the control device 13. The control unit 21 is designed such that it determines certain types T in the event-data E and provides a (type of) light pattern P matching to the detected type T of event-data E.

An illumination unit 22 comprising a linear arrangement of multiple light sources 23 that are controlled by the control unit 21 in order to emit a changing light pattern P provided by the control unit 21. This illumination unit 22 is here arranged on the scanner 2 of the MRI system 1.

In this example, the communication system 12 additionally comprises an ambient light sensor 24 and the control unit 21 is designed to control a basic brightness of a light pattern P depending on measurements of the ambient light sensor 24.

In this example, the communication system additionally comprises a light source 25 designed and arranged to illuminate the patient table 8 of the medical imaging system 1.

In this example, the communication system additionally comprises an acoustic output module 26 designed to emit sound patterns and/or, especially artificial, announcements, wherein the control unit 21 is designed to provide these sound patterns and/or announcements based on the event-data E and/or the provided light pattern P.

The MRI system 1 according to at least one example embodiment of the present invention, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
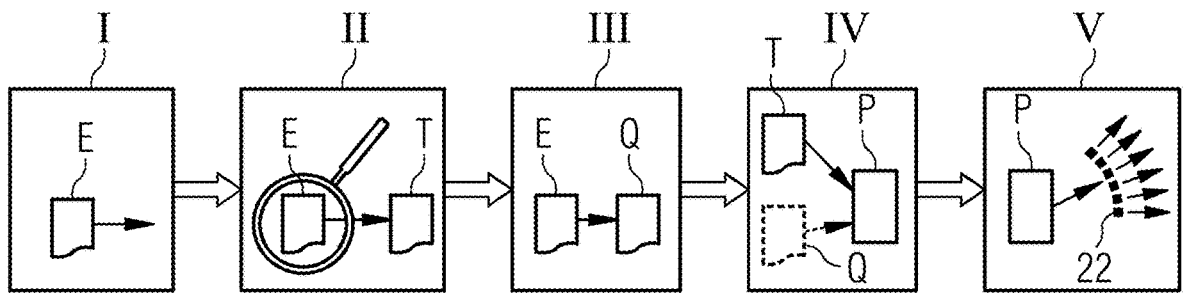
FIG. 2 shows a block diagram of the process flow of an embodiment according to the present invention.

FIG. 2 shows a block diagram of the process flow of a preferred communication method according to at least one example embodiment of the present invention for the medical imaging system 1, respectively the communication system 12 of FIG. 1.

In step I, event-data E is received from a medical imaging system 1 (see e.g. FIG. 1).

In step II, the type T of the event-data E is identified by examining the event-data E.

In step III, a quantitative value Q of the event-data E is identified. This step is optional.

In step IV, a light pattern P is provided depending on the identified type T and especially also the value Q of the event-data E.

In step V, the provided light pattern P is outputted with the illumination unit 22.

Also a sound pattern could be provided and outputted by an acoustic output module 26 as shown in FIG. 1, analogous to the above steps.

Figure 3:
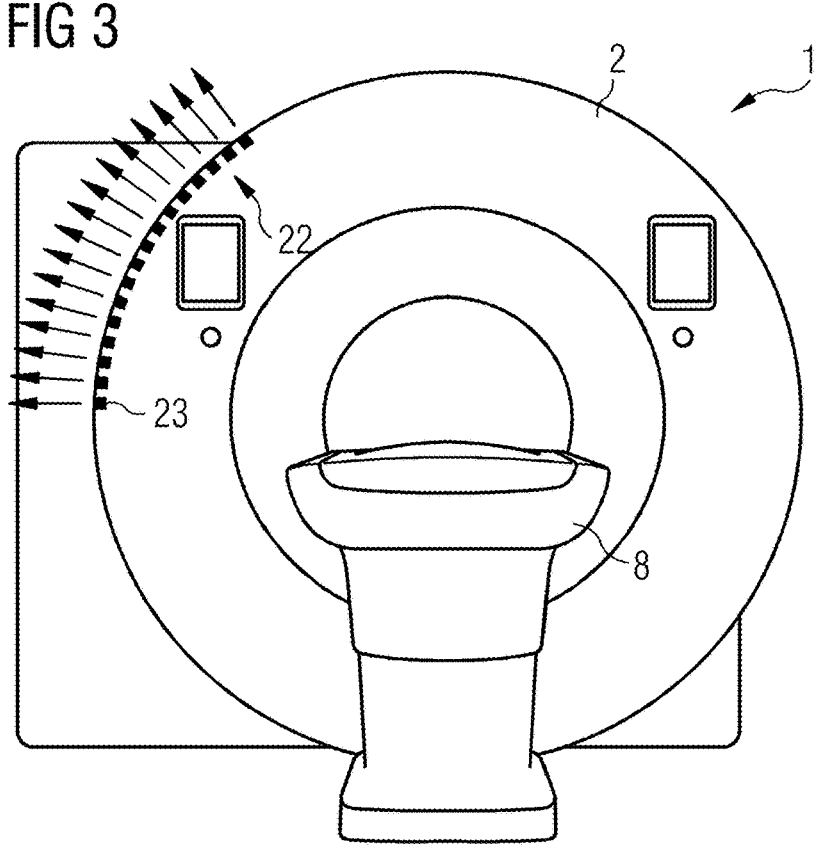
FIG. 3 shows an example embodiment of an illumination unit arranged on a MRI-system.

FIG. 3 shows an example of an illumination unit 22 arranged on a MRI-system 1. While in FIG. 1, the scanner 2 of the MRI system 1 is shown from the side, now it is shown a view into the scanner 2 from the front, looking along the patient table 8. The illumination unit 22 is arranged on the side of the scanner 2 following its curved shape and emitting light to the left side when activated. Every single light source 23 of the illumination unit 22 can be controlled separately.

Figure 4:
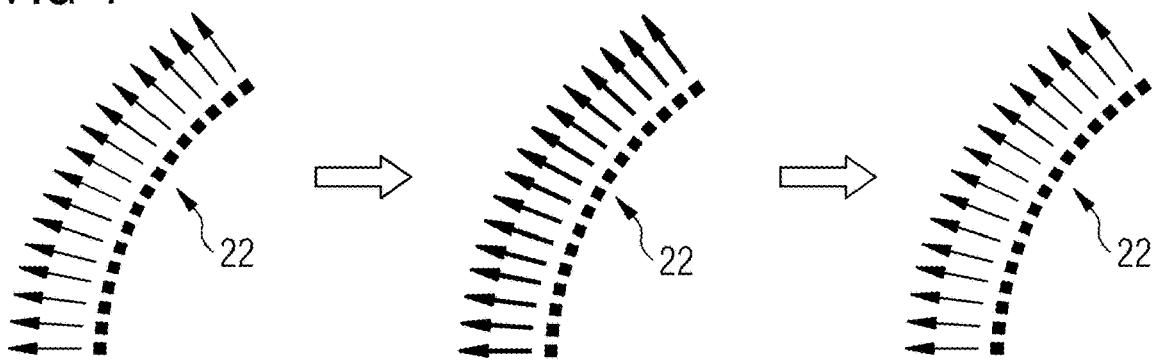
FIG. 4 shows an example of a light pattern.

FIG. 4 shows an example of a light pattern P that may be emitted by the illumination unit 22. The varying thickness of the arrows indicates different degrees of brightness. In the shown example, the dim light (left) grows brighter (middle) and is dimmed again (right). This pattern may be used for alarms (rapid blinking) or breath indication (brightness is changing synchronously with the breath).

Figure 5:
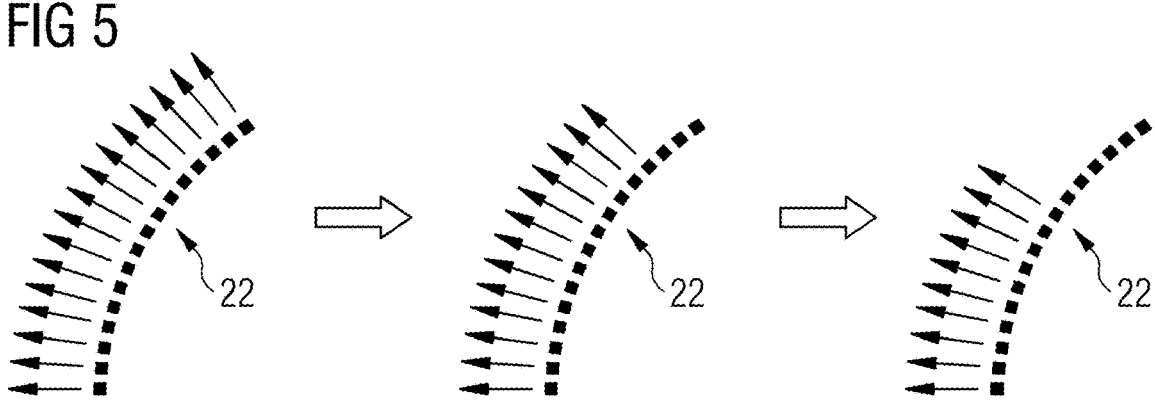
FIG. 5 shows another example of a light pattern.

FIG. 5 shows another example of a light pattern P that may be emitted by the illumination unit 22. In this example, the number of active light sources decreases from left to right. A countdown could be visualized with this pattern (left to right) or a progression of finishing a process (right to left or left to right).

Figure 6:
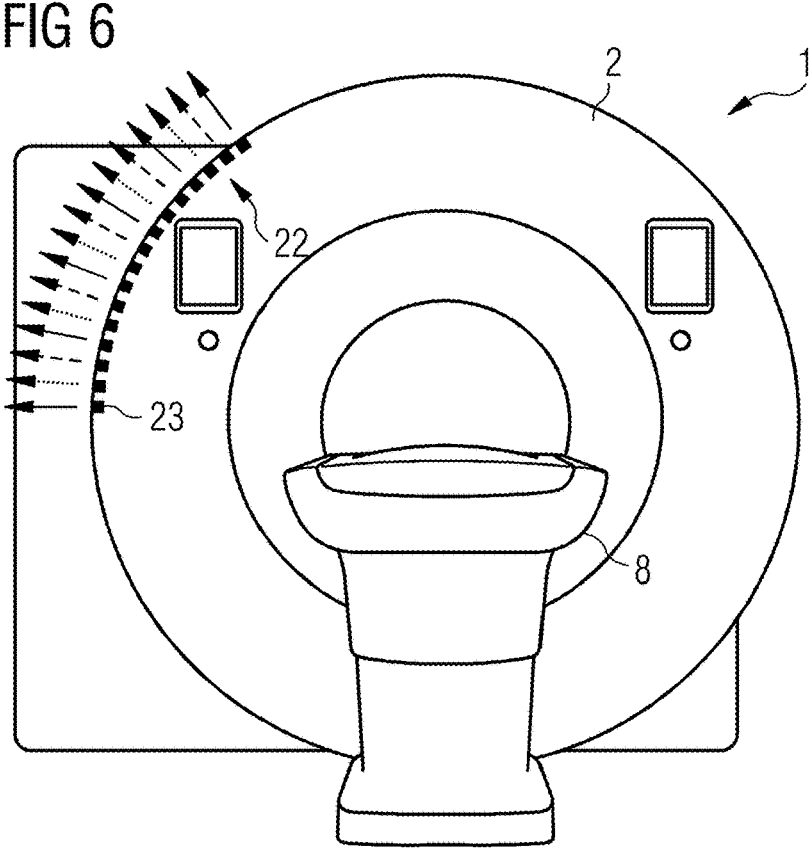
FIG. 6 shows a further example embodiment of an illumination unit arranged on a MRI-system.

FIG. 6 shows mainly the same embodiment as FIG. 3 with the difference that the illumination unit 22 here may emit colored light patterns P. The different colors are indicated with different line styles of the arrows (solid, dashed, dotted).

Figure 7:
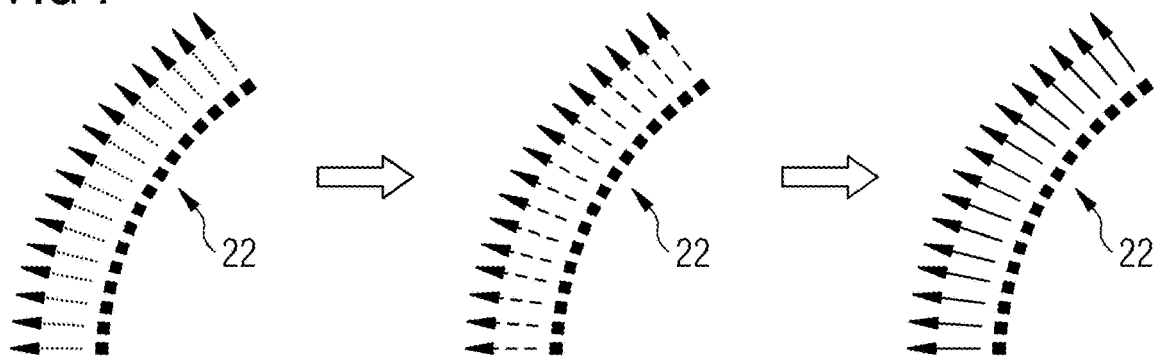
FIG. 7 shows a further example of a light pattern.

FIG. 7 shows another example of a colored light pattern P changing color, that may be emitted by the illumination unit 22. This could e.g. be used as indication for starting a process (red, yellow green like a traffic light).

Figure 8:
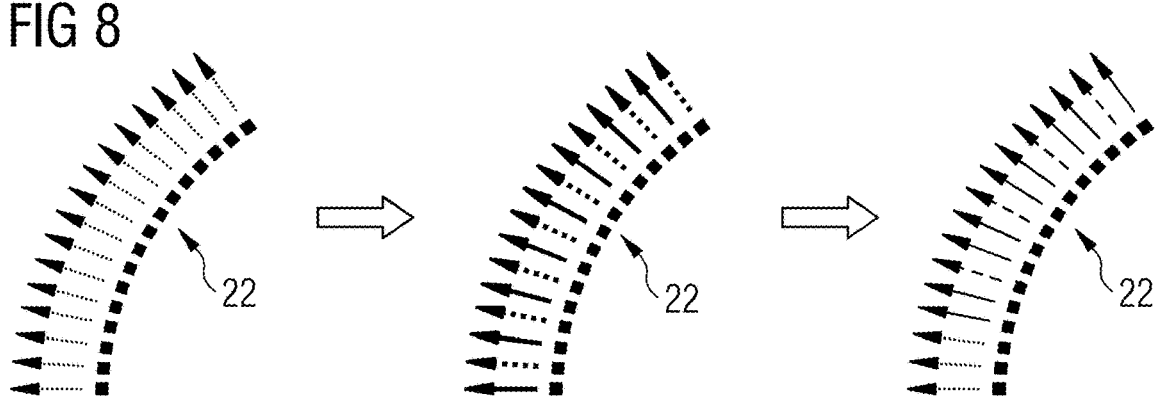
FIG. 8 shows a further example of a light pattern.

FIG. 8 shows a complex example of a light pattern P that may be emitted by the illumination unit 22. In this example the color as well as the brightness changes such that a chatoyant effect is produced. This could e.g. be used to indicate that the patient listens to a voice message.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A communication system for a medical imaging system, comprising:
   an illumination unit comprising a linear arrangement of multiple light sources; and
   a control unit configured to
      provide a first light pattern from a number of light patterns based on first event-data, the first event-data being among event-data corresponding to the medical imaging system, and different light patterns corresponding to different types of the event-data, and
      control the multiple light sources to emit the first light pattern.

2. The communication system according to claim 1, wherein
   the control unit is configured to control an intensity of individual light sources among the multiple light sources; and
   at least one of
      the illumination unit is configured to emit different colors and the control unit is configured to control an intensity of individual colors among the multiple light sources, or
      the control unit is configured to provide two or more light patterns contemporaneously.

3. The communication system according to claim 1, wherein the control unit is configured to assign an individual light pattern to one or more types of the event-data, the event data being associated with at least one of:
   an automatic sound output being provided to a user or a patient examined by the medical imaging system;
   physiological data;
   times or phases of an examination;
   errors, alarms or emergencies;
   a feedback to inputs of the user; or
   an indication of events automatically started.

4. The communication system according to claim 1, wherein the control unit comprises at least one of:
   a mapping table identifying an allocation of light patterns to types of the event-data; or
   a machine learning model trained for providing individual light patterns for the types of the event-data.

5. The communication system according to claim 1, wherein the control unit is configured to vary the first light patterns based on quantitative values of the first event-data.

6. The communication system according to claim 1, wherein the illumination unit is flexible or shaped such that the illumination unit is configured to be arranged on an outer surface of the medical imaging system.

7. The communication system according to claim 1, further comprising:
   an ambient light sensor, the control unit being configured to control a brightness of the first light pattern based on measurements of the ambient light sensor.

8. The communication system according to claim 1, further comprising:
   a number of additional light sources configured to illuminate areas of the medical imaging system, the areas including
      an area of a patient table of the medical imaging system, or
      an area adjacent to a-the patient table of the medical imaging system.

9. The communication system according to claim 1, further comprising:
   an acoustic output module configured to emit at least one of sound patterns or artificial announcements, wherein the control unit is configured to provide the at least one of sound patterns or artificial announcements based on at least one of (i) the first event-data or (ii) the first light pattern.

10. The communication system according to claim 1, wherein the control unit is configured to provide the first light pattern by:
    selecting the first light pattern from among the number of light patterns based on the first event-data, each of the number of light patterns corresponding to a different type of the event-data; or
    generating the first light pattern using the number of light patterns based on the first event-data, the different light patterns including the first light pattern, and the different types of the event-data including the first event-data.

11. The communication system according to claim 2, wherein the control unit is configured to assign an individual light pattern to one or more types of the event-data, the event data being associated with at least one of:
    an automatic sound output being provided to a user or a patient examined by the medical imaging system;
    physiological data;
    times or phases of an examination;
    errors, alarms or emergencies;
    a feedback to inputs of the user; or
    an indication of events automatically started.

12. The communication system according to claim 2, wherein the control unit comprises at least one of:
    a mapping table identifying an allocation of light patterns to types of the event-data; or
    a machine learning model trained for providing individual light patterns for the types of the event-data.

13. The communication system according to claim 3, wherein the control unit comprises at least one of:
    a mapping table identifying an allocation of light patterns to types of the event-data; or a machine learning model trained for providing individual light patterns for the types of the event-data.

14. The communication system according to claim 2, wherein the illumination unit is flexible or shaped such that the illumination unit is configured to be arranged on an outer surface of the medical imaging system.

15. The communication system according to claim 2, further comprising:
an ambient light sensor, the control unit being configured to control a brightness of a-the first light pattern based on measurements of the ambient light sensor.

16. A communication method, the method comprising:
identifying a type of first event-data, the first event-data being among event-data corresponding to a medical imaging system;
providing a first light pattern from a number of light patterns based on the type of the first event-data, different light patterns corresponding to different types of the event-data; and
outputting the first light pattern with an illumination unit, the illumination unit including a linear arrangement of multiple light sources.

17. The communication method according to claim 16, further comprising:
identifying at least one quantitative value of the first event-data; and
modifying the first light pattern according to the at least one quantitative value.

18. The communication method according to claim 16, wherein the providing the first light pattern is performed based on at least one of:
a patient listening to a message;
a message being output to a user;
physiological signals being received;
a countdown running;
a contrast agent being applied to the patient;
stages of an examination being reached;
an emergency or alarm occurring;
a user-input or a change of preferences occurring;
a movement of parts of the medical imaging system being initialized, occurring or being finished; or
actions automatically performed by the medical imaging system occurring.

19. A medical imaging system comprising the communication system according to claim 1.

20. A non-transitory computer-readable medium comprising a computer program that, when executed by a computing system or a control device for a medical imaging system, causes the computing system or the control device to perform a method, the method comprising:
identifying a type of first event-data, the first event-data being among event-data corresponding to a medical imaging system;
providing a first light pattern from a number of light patterns based on the type of the first event-data, different light patterns corresponding to different types of the event-data; and
outputting the first light pattern with an illumination unit, the illumination unit including a linear arrangement of multiple light sources.

21. The non-transitory computer-readable medium of claim 20, wherein the method further comprises:
identifying at least one quantitative value of the first event-data; and
modifying the first light pattern according to the at least one quantitative value.

* * * * *